United States Patent
Clark et al.

(10) Patent No.: US 6,376,500 B2
(45) Date of Patent: Apr. 23, 2002

(54) SUBSTITUTED 2-(4-PIPERIDYL)-4(3H)-QUINAZOLINONES AND 2-(4-PIPERIDYL)-4(3H)-AZAQUINAZOLINONES

(75) Inventors: Robin Douglas Clark, Palo Alto; Counde O'Yang, Sunnyvale, both of CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/803,078

(22) Filed: Mar. 8, 2001

Related U.S. Application Data

(62) Division of application No. 09/626,806, filed on Jul. 27, 2000, now Pat. No. 6,258,819.
(60) Provisional application No. 60/147,537, filed on Aug. 5, 1999, and provisional application No. 60/191,342, filed on Mar. 22, 2000.

(51) Int. Cl.[7] .................. A01N 43/54; A61K 31/505; C07D 471/00; C07D 419/00; C07D 421/00
(52) U.S. Cl. .................. 514/258; 514/259; 544/279; 544/284; 544/287
(58) Field of Search ................ 514/258, 259; 544/279, 284, 287

(56) References Cited

U.S. PATENT DOCUMENTS

| 4,522,945 A | 6/1985 | Vandenberk et al. |
| 5,196,425 A | 3/1993 | Vandenberk et al. |
| 5,321,028 A | 6/1994 | Vandenberk et al. ........ 514/258 |

FOREIGN PATENT DOCUMENTS

| JP | 08027149 | 1/1996 |
| WO | WO 94/01437 | 1/1994 |

OTHER PUBLICATIONS

Hori et al., Chem. Pharm. Bull, 1991, 39 (2), 367–371.
Teng et al., European Journal of Pharmacology, 1994, 265, 61–66.
Nishi et al., Urologia Internationalis, 1998, 61, 147–153.
Nishi et al., Journal of Urology 1998, 160, 196–205.
Yang et al. Journal of Pahrmacology and Exp. Therapeutics, 1998, 286(2), 841–847.
Hanft et al., British Journal of Pharmacology 1989, 97, 691–700.
Faure et al., Life Sciences 1994, 54(21), 1595–1605.
Furuya et al., Journal of Urology 1982, 128, 836–839.
Hatano et al., Br. J. Pharmacol. 1994, 113, 723–728.
Taniguchi et al., Archives of Pharmacology 1997, 355, 412–416.
Price et al., Journal of Urology 1993, 150, 546–551.
Marshall et al., Br. Journal of Pharmacology, 1995, 5, 781–786.

Primary Examiner—Mukund J. Shah
Assistant Examiner—Tamthom N. Truong
(74) Attorney, Agent, or Firm—Gloria Pfister

(57) ABSTRACT

This invention relates to compounds which are generally alpha$_{1A/B}$-receptor antagonists and which are represented by Formula I:

(I)

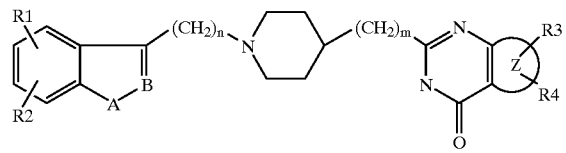

wherein the substituents are as defined in the specification; or pharmaceutically acceptable salts, hydrates, or N-oxides thereof. The invention further relates to pharmaceutical compositions containing such compounds, methods for their use as therapeutic agents, and a process for their preparation.

28 Claims, No Drawings

SUBSTITUTED 2-(4-PIPERIDYL)-4(3H)-QUINAZOLINONES AND 2-(4-PIPERIDYL)-4(3H)-AZAQUINAZOLINONES

CROSS-REFERENCE TO RELATED INVENTIONS

This application is a divisional of pending application Ser. No. 09/626,806, filed Jul. 27, 2000 is now U.S. Pat. No. 6,258,819, and this application also claims the benefit under 35 U.S.C. 119(e) of U.S. Provisional Application Nos. 60/147,537, filed Aug. 5, 1999 and 60/191,342, filed Mar. 22, 2000; all applications are hereby incorporated by reference in its entirety.

FIELD OF THE INVENTION

This invention relates to substituted 2-(4-piperidyl)-4(3H)-quinazolinone and 2-(4-piperidyl)-4(3H)-azaquinazolinone derivatives, associated pharmaceutically acceptable salts, hydrates and N-oxides thereof, associated pharmaceutical compositions, and methods for use as $alpha_{1A/B}$-adrenergic receptor ($alpha_{1A/B}$-adrenoceptor) antagonists.

BACKGROUND OF THE INVENTION

Alpha1-adrenergic receptors are G-protein coupled transmembrane receptors that mediate various actions of the sympathetic nervous system through the binding of the catecholamines, epinephrine and norepinephrine. Currently, several subtypes of the alpha $_1$-adrenergic receptors are known to exist for which the genes have been cloned: alpha $_{1A}$ (previously known as alpha $_{1C}$), alpha $_{1B}$ and alpha $_{1D}$. The existence of an additional subtype, the alpha $_{1L}$-adrenergic receptor subtype, has been proposed; however, the gene for the alpha $_{1L}$-adrenergic receptor subtype has yet to be cloned.

Alpha1-adrenoceptor antagonists have been shown in numerous clinical studies to be effective in relieving the symptoms associated with benign prostatic hypertrophy (BPH). However, these compounds are all non-subtype-selective, and have the potential to cause significant side-effects, particularly cardiovascular effects such as postural hypotension, and CNS effects including aesthenia (tiredness). These effects can limit dosing, and thus clinical efficacy in reducing symptoms associated with BPH.

Pharmacological studies resulting in the subdivision of $alpha_1$-adrenoceptors into $alpha_{1A}$-, $alpha_{1B}$- and $alpha_{1D}$-adrenoceptors have led to the suggestion that development of subtype-selective antagonists may allow improved symptomatic treatment of BPH/unstable bladder with a lower incidence of dose-limiting side-effects. An $alpha_{1A}$-subtype-selective antagonist may, via a selective and significant decrease in outlet resistance, lead to improved pharmacotherapy for BPH. However, it must be noted that in BPH, it is often the irritative symptoms which prompt the patient to seek treatment, and that these irritative symptoms may be present even in patients with no demonstrable obstruction (i.e. normal urine flow rates). By combining both $alpha_{1A}$- and $alpha_{1B}$-subtype-selectivity in a drug molecule, a reduction of both obstructive and irritative symptoms in patients with BPH may be achieved. Lower levels or lack of $alpha_{1D}$-adrenoceptor antagonism should lead to reduced or fewer side effects than those associated with the use of non-subtype-selective agents.

All publications, patents, and patent applications cited herein, whether supra or infra, are each hereby incorporated by reference in its entirety.

DESCRIPTION OF THE RELATED ART

U.S. application No. 60/124,721 assigned to Syntex (U.S.A.) Inc. refers to certain methods for screening compounds to identify certain $alpha_{1B}$-adrenergic receptor ligands that bind to the $alpha_{1B}$-adrenergic receptor to provide an analgesic effect.

U.S. Pat. No. 4,522,945 assigned to Janssen Pharm. refers to certain (piperdinylalkyl)-quinazoline derivatives as serotonin antagonists.

U.S. Pat. No. 5,196,425 and U.S. Pat. No. 5,321,028 assigned to Janssen Pharm. refer to certain antihypertensive 3-piperidinyl-indazole derivatives as antagonists of neurotransmitters.

PCT published application WO 9401437 assigned to Janssen Pharm. refers to certain benzofuranyl and benzothienyl piperidinyl derivatives as antidopaminergic agents.

Japanese patent application JP 08027149 assigned to Meiji Seika Kaisha Ltd. refers to certain fused pyrimidinone derivatives useful as antipsychotic drugs.

Hori et al., Chem. Pharm.Bull. 1991, 39(2), 367–371, refer to certain 4-alkoxy-2-(1-piperazinyl)quinazoline derivatives useful as nootropic agents.

Teng et al., European Journal of Pharmacology 1994, 265, 61–66, refer to certain functional identification of $alpha_1$-adrenoceptor subtypes in human prostate.

Nishi et al., Urologia Internationalis 1998, 61, 147–153, refer to certain properties of alpha-1 adrenergic receptors in the rat prostate.

Nishi et al., Journal of Urology 1998, 160, 196–205, refer to certain characterization, localization and distribution of $alpha_1$-adrenoceptor subtype in male rabbit urethra.

Yang et al, Journal of Pharmacology and Experimental Therapeutics 1998, 286(2), 841–847, refer to certain murine $alpha_1$-adrenoceptor subtypes.

Hanft et al, British Journal of Pharmacology 1989, 97, 691–700, refer to certain subclassification of $alpha_1$-adrenoceptor recognition sites by urapidil derivatives and other selective antagonists.

Faure et al., Life Sciences 1994, 54 (21), 1595–1605, refer to certain identification of $alpha_1$-adrenoceptor subtypes present in the human prostate.

Furuya et al., Journal of Urology 1982, 128, 836–839, refer to certain alpha-adrenergic activity and urethral pressure in prostatic zone in benign prostatic hypertrophy.

Hatano etal., Br. J. Pharmacol. 1994, 113, 723–728, refer to certain pharmacological evidence of distinct $alpha_1$-adrenoceptor subtypes mediating the contraction of human prostatic urethra and peripheral artery.

Taniguchi et al., Archives of Pharmacology 1997, 355, 412–416, refer to certain identification of $alpha_1$-adrenoceptor subtypes in the human prostatic urethra.

Price et al., Journal of Urology 1993, 150, 546–551, refer to certain identification, quantification, and localization of mRNA for three distinct $alpha_1$-adrenergic receptor subtypes in human prostate.

Marshall et al., Br. Journal of Pharmacology 1995, 5, 781–786, refer to certain noradrenaline contractions of human prostate mediated by $alpha_{1A}$-($_{1C}$-) adrenoceptor subtype.

SUMMARY OF THE INVENTION

This invention relates to compounds comprising Formula I:

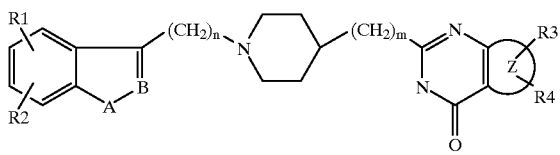

wherein:
- A—B is independently in each occurrence NH—C, NH—N, O—C, or S—C;
- Z is a benzene or a pyridine ring;
- $R^1$, $R^2$, $R^3$, and $R^4$ are each independently in each occurrence hydrogen, halogen, lower alkyl, lower alkoxy, hydroxy, cyano, nitro, trifluoromethyl, CO—NR'R", NR'R", or NR'—CO—NR'R";
- R' and R" are each independently in each occurrence hydrogen or lower alkyl;
- m is an integer ranging from 0 to 3 inclusive;
- n is an integer ranging from 1 to 6 inclusive; or pharmaceutically acceptable salts, hydrates or N-oxides thereof.

In a more preferred embodiment, m is 0. More preferably m is 0 and n is 2.

In another preferred embodiment, $R^1$, $R^2$, $R^3$, and $R^4$ are each independently in each occurrence hydrogen, halogen, or lower alkoxy.

In another preferred embodiment Z is a benzene ring.

In another preferred embodiment Z is a pyridine ring.

In a preferred embodiment the compound is 2-{1-[2-(1H-indol-3-yl)-ethyl]-piperidin-4-yl-3H-quinazolin-4-one; 6-chloro-2-{1-[2-(1H-indol-3-yl)-ethyl]-piperidin-4-yl}-3H-quinazolin-4-one; 7-chloro-2-(1-[2-(1H-indol-3-yl)-ethyl]-piperidin-4-yl}-3H-quinazolin-4-one; 7-fluoro-2-{1-[2-(1H-indol-3-yl)-ethyl]-piperidin-4-yl}-3H-quinazolin 4-one; 6,7-difluoro-2-{1-[2-(1H-indol-3-yl)-ethyl]-piperidin-4-yl}-3H-quinazolin-4-one; 2-{1-[2-(6-fluoro-1H-indol-3-yl)-ethyl]-piperidin-4-yl}-3H-quinazolin-4-one; 5-chloro-2-{1-[2-(6-fluoro-1H-indol-3-yl)-ethyl]-piperidin-4-yl}-3H-quinazolin-4-one; 6-chloro-2-{1-[2-(6-fluoro-1H-indol-3-yl)-ethyl]-piperidin-4-yl}-3H-quinazolin-4-one; 7-chloro-2-{1-[2-(6-fluoro-1H-indol-3-yl)-ethyl]-piperidin-4-yl}-3H-quinazolin-4-one; 5-fluoro-2-{1-[2-(6-fluoro-1H-indol-3-yl)-ethyl]-piperidin-4-yl}-3H-quinazolin-4-one; 6-fluoro-2-{1-[2-(6-fluoro-1H-indol-3-yl)-ethyl]-piperidin-4-yl}-3H-quinazolin-4-one; 7-fluoro-2-{1-[2-(6-fluoro-1H-indol-3-yl)-ethyl]-piperidin-4-yl}-3H-quinazolin-4-one; 6,7-difluoro-2-{1-[2-(6-fluoro-1H-indol-3-yl)-ethyl]-piperidin-4-yl}-3H-quinazolin-4-one; 2-{1-[2-(6-fluoro-1H-indol-3-yl)-ethyl]-piperidin-4-yl}-3H-quinazolin-4-one; or pharmaceutically acceptable salts, hydrates or N-oxides thereof; more preferably the compound is 2-{1-[2-(1H-indol-3-yl)-ethyl]-piperidin-4-yl}-3H-quinazolin-4-one; 2-{1-[2-(6-fluoro-1H-indol-3-yl)-ethyl]-piperidin-4-yl}-3H-quinazolin-4-one; 7-fluoro-2-{1-[2-(6-fluoro-1H-indol-3-yl)-ethyl]-piperidin-4-yl}-3H-quinazolin-4-one; 6-fluoro-2-{1-[2-(6-fluoro-1H-indol-3-yl)-ethyl]-piperidin-4-yl}-3H-quinazolin-4-one; 6,7-difluoro-2-{1-[2 -(6-fluoro-1H-indol-3-yl)-ethyl]-piperidin-4-yl}-3H-quinazolin-4-one; or pharmaceutically acceptable salts, hydrates or N-oxides thereof.

This invention further relates to pharmaceutical compositions containing a therapeutically effective amount of a compound or compounds of Formula (I), or pharmaceutically acceptable salts, hydrates or N-oxides thereof, in admixture with one or more suitable carriers.

In a preferred embodiment the method of treating a subject comprises administering to the subject a therapeutically effective amount of one or more compounds of Formula (I) or pharmaceutically acceptable salts, hydrates or N-oxides thereof, in admixture with one or more suitable carriers.

In another preferred embodiment the method of treating a subject comprises administering to the subject a therapeutically effective amount of the pharmaceutical composition containing at least one compound of Formula (I) or pharmaceutically acceptable salts, hydrates or N-oxides thereof, in admixture with one or more suitable carriers.

In another preferred embodiment the method of treating a subject comprises administering to the subject a thereapeutically effective amount of the pharmaceutical composition containing an $alpha_1$-adrenoceptor antagonist; more preferably the pharmaceutical composition contains an $alpha_{1A/B}$-adrenoceptor antagonist.

In a preferred embodiment, the compounds of Formula (I), or the pharmaceutical compositions thereof, are suitable for administration to a subject having a disease state which is alleviated by treatment with an $alpha_1$ antagonist. More preferably, the compounds of Formula (I), or the pharmaceutical compositions thereof, are suitable for administration to a subject having a disease state which is alleviated by treatment with an antagonist combining $alpha_{1A}$- and $alpha_{1B}$-subtype selectivity.

The invention further relates to a method for treating a subject having a disease state that is alleviated by treatment with an $alpha_1$-antagonist. More preferably, the invention relates to a method for treating a subject having a disease state that is alleviated by treatment with an antagonist, combining both $alpha_{1A}$- and $alpha_{1B}$-subtype-selectivity, which comprises administering to such a subject a therapeutically effective amount of a compound or compounds Formula I, or pharmaceutically acceptable salts, hydrates or N-oxides thereof.

In a preferred embodiment, the subject has a disease state comprising disorders and symptoms of the urinary tract such as incontinence, benign prostatic hypertrophy (BPH), prostatitis, detrusor hyperreflexia, outlet obstruction, urinary frequency, nocturia, urinary urgency, overactive bladder, pelvic hypersensitivity, urge incontinence, urethritis, prostatodynia, cystitis, idiophatic bladder hypersensitivity, and the like. More preferably, the disease state comprises disorders and symptoms of obstruction of the urinary tract such as benign prostatic hypertrophy and the irritative symptoms associated with it. In another preferred embodiment, the subject has a disease state that is alleviated by analgesic/antihyperalgesic therapies for treating pain, including symptoms of acute pain, inflammatory pain, neuropathic pain, cancer pain, acute pain, chronic pain, or complex regional pain syndromes.

In a preferred embodiment, a process comprises reacting a compound having a general formula

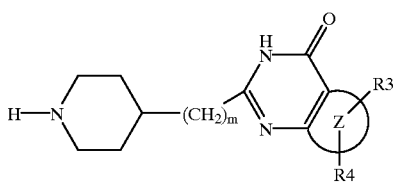

with a compound of general formula

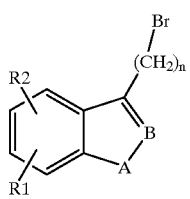

to provide a compound of the general formula

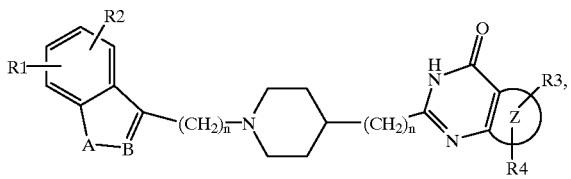

wherein $R_1$, $R_2$, $R_3$, $R_4$, A, B, Z, m and n are as defined herein.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a," "an" and "the" include plural referents unless the context clearly dictates otherwise.

"Alkyl" means the monovalent linear or branched saturated hydrocarbon radical, consisting solely of carbon and hydrogen atoms, having from one to twenty carbon atoms inclusive, unless otherwise indicated. Examples of an alkyl radical include, but are not limited to, methyl, ethyl, propyl, isopropyl, isobutyl, sec-butyl, tert-butyl, pentyl, n-hexyl, octyl, dodecyl, tetradecyl, eicosyl, and the like.

"Lower alkyl" means the monovalent linear or branched saturated hydrocarbon radical, consisting solely of carbon and hydrogen atoms, having from one to six carbon atoms inclusive, unless otherwise indicated. Examples of a lower alkyl radical include, but are not limited to, methyl, ethyl, propyl, isopropyl, tert-butyl, n-butyl, n-hexyl, and the like.

"Lower alkoxy" means the radical —O—R, wherein R is a lower alkyl radical as defined above. Examples of a lower alkoxy radical include, but are not limited to, methoxy, ethoxy, isopropoxy, and the like.

"Halogen" means the radical fluoro, bromo, chloro, and/or iodo.

"Optional" or "optionally" means that the subsequently described event or circumstance may but need not occur, and that the description includes instances where the event or circumstance occurs and instances in which it does not. For example, "optional bond" means that the bond may or may not be present, and that the description includes single, double, or triple bonds.

"Leaving group" means the group with the meaning conventionally associated with it in synthetic organic chemistry, i.e., an atom or group displaceable under alkylating conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Protective group" or "protecting group" means the group which selectively blocks one reactive site in a multifunctional compound such that a chemical reaction can be carried out selectively at another unprotective reactive site in the meaning conventionally associated with it in synthetic chemistry.

"Amino-protecting group" means the protecting group that refers to those organic groups intended to protect the nitrogen atom against undesirable reactions during synthetic procedures and includes, but is not limited to, acetyl, benzyl, benzyloxycarbonyl (carbobenzyloxy, CBZ), p-methoxybenzyloxycarbonyl, p-nitrobenzyloxycarbonyl, tert-butoxycarbonyl (BOC), trifluoroacetyl, and the like. Certain protective groups may be preferred over others due to their convenience or relative ease of removal. In a preferred mode either acetyl or BOC are used as the amino-protecting groups because of their relative ease of removal.

"Deprotection" or "deprotecting" means the process by which a protective group is removed after the selective reaction is completed. Deprotecting reagents for protected amino groups include but are not limited to hydrogenolysis and treatment with acids. Removal of the acetyl group is affected by treatment with strong aqueous acid, including but not limited to hydrochloric acid. Removal of the tert-butoxycarbonyl (BOC) protecting group is accomplished by treatment with acid including but not limited to, trifluoroacetic acid in a chlorinated hydrocarbon such as, for example, dichloromethane or dichloroethane, or by treatment with alcoholic mineral acid, such as hydrochloric acid in ethanol. Removal of the carbobenzyloxy (CBZ) group is accomplished for example with strong acid including but not limited to hydrobromic acid in acetic acid, or hydrogenolysis.

"Inert organic solvent" or "inert solvent" means the solvent inert under the conditions of the reaction being described in conjunction therewith, including for example, benzene, toluene, acetonitrile, tetrahydrofuran, N,N-dimethylformamide, chloroform ($CHCl_3$), methylene chloride or dichloromethane ($CH_2Cl_2$), dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" of a compound means a salt that is pharmaceutically acceptable, as defined above, and that possesses the desired pharmacological activity of the parent compound. Such salts include:

1. acid addition salts formed with inorganic acids such as hydrochloric acid, hydrobromic acid, trifluoroacetic acid, sulfuric acid, nitric acid, phosphoric acid, and the like; or formed with organic acids such as acetic acid, benzenesulfonic acid, benzoic acid, camphorsulfonic acid, p-chlorobenzenesulfonic acid, cinnamic acid, citric acid, cylcopentanepropionic acid, ethanesulfonic acid, 1,2-ethanedisulfonic acid, fumaric acid, glucoheptonic acid, gluconic acid, glutamic acid, glycolic acid, hexanoic acid, heptanoic acid, o-(hydroxybenzoyl)benzoic acid, hydroxynaphtoic acid, 2-hydroxyethanesulfonic acid, lactic acid, lauryl sulfuric acid, maleic acid, malic acid, malonic acid, mandelic acid, methanesulfonic acid, 4-methylbicyclo[2.2.2]oct-2-ene-1-carboxylic acid, 4,4'-methylenebis(3-hydroxy-2-ene-1-carboxylic acid), muconic acid, 2-naphthalenesulfonic acid, oxalic acid, 3-phenylpropionic acid, propionic acid, pyruvic acid, salicylic acid, stearic acid, succinic acid, tartaric acid, tertiary butylacetic acid, p-toluenesulfonic acid, trimethylacetic acid, and the like; or 2. salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide. The preferred pharmaceutically acceptable salts are the salts formed from hydrochloric acid, and trifluoroacetic acid.

"N-oxide" means an internal salt formed when one or several nitrogen atoms of aliphatic or aromatic amines are oxidated to the N-oxide form, in particular those N-oxides formed upon the oxidation of tertiary cyclic amines to give a chemically stable tertiary cyclic amine N-oxides, e.g., the piperidine N-oxide.

"Pharmaceutically acceptable hydrates" means the hydrates, which are pharmaceutically acceptable, as defined above, and which possess the desired pharmacological activity. Such hydrates are formed by the combination of one or more molecules of water with one of the substances, in which the water retains its molecular state as $H_2O$, such combination being able to form one or more than one hydrate.

"Subject" means mammals and non-mammals. Mammals means any member of the Mammalia class including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

A "therapeutically effective amount" means an amount of a compound that, when administered to a subject for treating a disease, is sufficient to effect such treatment for the disease. The "therapeutically effective amount" will vary depending on the compound, the disease state being treated, the severity or the disease treated, the age and relative health of the subject, the route and form of administration, the judgement of the attending medical or veterinary practitioner, and other factors.

The term "pharmacological effect" as used herein encompasses effects produced in the subject that achieve the intended purpose of a therapy. In one preferred embodiment, a pharmacological effect means that pain symptoms of the subject being treated are prevented, alleviated, or reduced. For example, a pharmacological effect would be one that results in the reduction of pain in a treated subject. In another preferred embodiment, a pharmacological effect means that disorders or symptoms of the urinary tract of the subject being treated are prevented, alleviated, or reduced. For example, a pharmacological effect would be one that results in the prevention or reduction of benign prostatic hypertrophy, outlet obstruction, incontinence or pelvic hypersensitivity in a treated subject.

"Disease state" means any disease, condition, symptom, or indication.

"Treating" or "treatment" of a disease state includes:
1. preventing the disease state, i.e. causing the clinical symptoms of the disease state not to develop in a subject that may be exposed to or predisposed to the disease state, but does not yet experience or display symptoms of the disease state,
2. inhibiting the disease state, i.e., arresting the development of the disease state or its clinical symptoms, or
3. relieving the disease state, ie., causing temporary or progressive regression of the disease state or its clinical symptoms.

"Pro-drug" means a pharmacologically inactive form of a compound which must be metabolized in vivo by a subject after administration into a pharmacologically active form of the compound in order to produce the desired pharmacological effect. After administration to the subject, the pharmacologically inactive form of the compound is converted in vivo under the influence of biological fluids or enzymes into a pharmacologically active form of the compound. Although metabolism occurs for many compounds primarily in the liver, almost all other tissues and organs, especially the lung, are able to carry out varying degrees of metabolism. Pro-drug forms of compounds may be utilized, for example, to improve bioavailability, mask unpleasant characteristics such as bitter taste, alter solubility for intravenous use, or to provide site-specific delivery of the compound. Reference to a compound herein includes pro-drug forms of a compound.

"$Alpha_1$-adrenergic receptors", "$alpha_{1A}$-adrenergic receptors" (previously known as "$alpha_{1C}$-adrenergic receptors"), "$alpha_{1B}$-adrenergic receptors", "$alpha_{1D}$-adrenergic receptors" or "$alpha_{1L}$-adrenergic receptors", used interchangeably with "$alpha_1$-adrenoceptors", "$alpha_{1A}$-adrenoceptors" (previously known as "$alpha_{1C}$-adrenoceptors receptors"), "$alpha_{1B}$-adrenoceptors", "$alpha_{1D}$-adrenoceptors" or "$alpha_{1L}$-adrenoceptors", respectively, refers to a molecule conforming to the seven membrane-spanning G-protein receptors, which under physiologic conditions mediate various actions, for example, in the central and/or peripheral sympathetic nervous system through the binding of the catecholamines, epinephrine and norepinephrine. Examples of physiological effects mediated by "$alpha_1$-adrenoceptors" include, but are not limited to, control of blood pressure, glycogenolysis, growth and hypertrophy of cardiac myocytes, contractility of the urinary tract, and the like.

The term "$alpha_1$-adrenergic receptor subtype" used interchangeably with "$alpha_1$-adrenoceptor subtype" refers to a distinct member of the class of $alpha_1$-adrenoceptors, selected from the "$alpha_{1A}$-(previously known as $alpha_{1C}$-), $alpha_{1B}$-, $alpha_{1D}$-, or $alpha_{1L}$-receptors". The subtypes have been distinguished based on differential binding profiles of ligands, such as the agonist, oxymetazoline, and the antagonists, WB4101 and phentolamine. Furthermore, the genes encoding the $alpha_{1A}$-(previously known as $alpha_{1C}$-), $alpha_{1B}$-, and $alpha_{1D}$-subtypes have been isolated and cloned. The existence of an additional subtype, the $alpha_{1L}$-adrenegic receptor subtype, has been proposed; however, the gene for the $alpha_{1L}$-adrenergic receptor subtype has not yet been cloned.

The term "specific alpha$_1$-adrenergic receptor" as used herein, refers to a distinct member of the group or class of adrenoceptors, which may be selected from the human alpha$_{1A}$-(previously known as alpha$_{1C}$-), alpha$_{1B}$-, alpha$_{1D}$-, and alpha$_{1L}$-adrenergic receptors. Preferred species from which may be derived or isolated alpha$_1$-adrenergic receptor subtype polypeptides, genes encoding and alpha$_1$-adrenergic receptor subtype, and/or cells, tissues and organs that express one or more alpha$_1$-adrenergic receptor subtype, include human, bovine, rat, murine, porcine, and the like. A more preferred species is human.

"Alpha$_{1B}$-adrenergic receptor" means the specific alpha$_1$-adrenoceptor expressed in numerous tissues, most notably in the liver, heart, and cerebral cortex. Alpha$_{1B}$-adrenoceptors are also present in areas of the spinal cord, which receive input from sympathetic neurons originating in the pontine micturition center, and are presumed to be involved in the regulation of bladder function.

"Alpha$_{1A/B}$-adrenergic receptor antagonist" means a compound that combines both alpha$_{1A}$- and alpha$_{1B}$-receptor selectivity, with lower or no alpha$_{1D}$-receptor selectivity.

"Trauma" means any wound or injury. Trauma can produce, for example, acute and/or chronic pain, inflammatory pain, and neuropathic pain.

"Pain" means the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (*Dorland's Illustrated Medical Dictionary*, 28$^{th}$ Edition, W. B. Saunders Company, Philadelphia, Pa.). The goal of treatment of pain is to reduce the degree of severity of pain perceived by a treatment subject.

"Neuropathic pain" means the pain resulting from functional disturbances and/or pathological changes as well as non inflammatory lesions in the peripheral nervous system. Examples of neuropathic pain include, but are not limited to, thermal or mechanical hyperalgesia, thermal or mechanical allodynia, diabetic pain, entrapment pain, and the like.

"Hyperalgesia" means the pain that results from an excessive sensitiveness or sensitivity.

"Allodynia" means the pain that results from a non-noxious stimulus to the skin. Examples of allodynia include, but are not limited to, cold allodynia, tactile allodynia, and the like.

"Complex regional pain syndromes" means the pain that includes, but is not limited to, reflex sympathetic dystrophy, causalgia, sympathetically maintained pain, and the like.

"Causalgia" means the burning pain, often accompanied by trophic skin changes, due to injury of a peripheral nerve.

"Nociception" means the pain sense. "Nociceptor" means the structure that mediates nociception. Nociception may be the result of a physical stimulus, such as, mechanical, electrical, thermal, or a chemical stimulus. Most nociceptors are in either the skin or the viscera walls.

"Analgesia" means the relief of pain without the loss of consciousness. An "analgesic" is an agent or drug useful for relieving pain, again without the loss of consciousness.

"Disorders of the urinary tract" or "uropathy" used interchangeably with "symptoms of the urinary tract" means the pathologic changes in the urinary tract. Symptoms of the urinary tract include overactive bladder (also known as detrusor hyperactivity), outlet obstruction, outlet insufficiency, and pelvic hypersensitivity. Examples of urinary tract disorders include, but are not limited to, incontinence, benign prostatic hypertrophy (BPH), prostatitis, detrusor hyperreflexia, outlet obstruction, urinary frequency, nocturia, urinary urgency, overactive bladder, pelvic hypersensitivity, urge incontinence, urethritis, prostatodynia, cystitis, idiophatic bladder hypersensitivity, and the like.

"Overactive bladder" or "Detrusor hyperactivity" includes, but is not limited to, the changes symptomatically manifested as urgency, frequency, reduced bladder capacity, incontinence episodes, and the like; the changes urodynamically manifested as changes in bladder capacity, micturition threshold, unstable bladder contractions, sphincteric spasticity, and the like; and the symptoms usually manifested in detrusor hyperreflexia (neurogenic bladder), in conditions such as outlet obstruction, outlet insufficency, pelvic hypersensitivity, or in idiopathic conditions such as detrusor instability, and the like.

"Outlet obstruction" includes, but is not limited to, benign prostatic hypertrophy (BPH), urethral stricture disease, tumors and the like. It is usually symptomatically manifested as obstructive (low flow rates, difficulty in initiating urination, and the like), and irritative (urinary urge and frequency, suprapubic pain, nocturia, and the like).

"Outlet insufficiency" includes, but is not limited to, urethral hypermobility, intrinsic sphincteric deficiency, or mixed incontinence. It is usually symptomatically manifested as stress incontinence.

"Pelvic Hypersensitivity" includes but is not limited to pelvic pain, interstitial (cell) cystitis, prostadynia, prostatis, vulvadynia, urethritis, orchidalgia, and the like. It is symptomatically manifested as pain, inflammation or discomfort referred to the pelvic region, and usually includes symptoms of overactive bladder.

Nomenclature

The naming and numbering of the compounds of this invention is illustrated below:

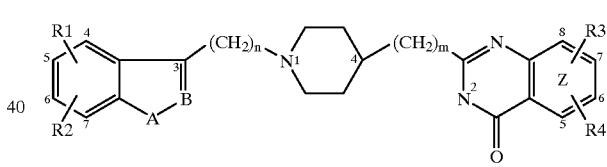

(I)

In general, the nomenclature used in this Application is based on Autonom, a Beilstein Institute computerized system for the generation of IUPAC systematic nomenclature. However, because a strict adherence to these recommendations would result in the names changing substantially when only a single substituent is changed, compounds have been named in a manner that maintains consistency of nomenclature for the basic molecule.

For example, a compound of Formula (I) wherein R$^1$ is 6-F, R$^3$ is 6-Cl, R$^2$ and R$^4$ are hydrogen, m is 0, n is 2, A—B is NH—C, and Z is benzene is named 6-chloro-2-{1-[2-(6-fluoro-1H-indol-3-yl)-ethyl]-piperidin-4-yl}-3H-quinazolin-4-one.

For example, a compound of Formula (I) wherein R$^1$ is 6-F, R$^2$, R$^3$ and R$^4$ are hydrogen, m is 0, n is 2, A—B is NH—C, and Z is pyridine is named 8-aza-2-{1-[2-(6-fluoro-1H-indol-3-yl)-ethyl]-piperidin-4-yi}-3H-quinazolin-4-one.

Preferred Compounds

Among compounds of the present invention set forth in the Summary of the Invention, certain compounds of Formula I are preferred.

For example, preferred compounds of Formula I include those wherein m is preferably 0; more preferably, m is 0 and n is 2.

Preferred compounds of Formula I also include those wherein $R^1$, $R^2$, $R^3$, and $R^4$ are each independently in each occurrence hydrogen, halogen, or lower alkoxy.

Preferred compounds of Formula I also include those wherein A—B is independently in each occurrence NH—N or NH—C, and more preferably independently in each occurrence NH—C.

Other preferred compounds of the present invention include the pharmaceutically acceptable salts of the compounds of the present invention wherein the pharmaceutically acceptable salts are formed from hydrochloric acid, phosphoric acid, trifluoroacetic acid, fumaric acid, tartaric acid, succinic acid, malonic acid, p-toluenesulfonic acid, succinic acid, or sulfuric acid, more preferably the salts are formed from hydrochloric acid or trifluoroacetic acid.

Exemplary particularly preferred compounds of Formula (I) include:
2-{1-[2-(1H-indol-3-yl)-ethyl]-piperidin-4-yl}-3H-quinazolin-4-one 10;
6-chloro-2-{1-[2-(1H-indol-3-yl)-ethyl]-piperidin-4-yl}-3H-quinazolin-4-one 14;
7-chloro-2-{1-[2-(1H-indol-3-yl)-ethyl]-piperidin-4-yl}-3H-quinazolin-4-one 16;
7-fluoro-2-{1-[2-(1H-indol-3-yl)-ethyl]-piperidin-4-yl}-3H-quinazolin-4-one 22;
6,7-difluoro-2-{1-[2-(1H-indol-3-yl)-ethyl]-piperidin-4-yl}-3H-quinazolin-4-one 24;
2-{1-[2-(6-fluoro-1H-indol-3-yl)-ethyl]-piperidin-4-yl}-3H-quinazolin-4-one 66;
5-chloro-2-{1-[2-(6-fluoro-1H-indol-3-yl)-ethyl]-piperidin-4-yl}-3H-quinazolin-4-one 68;
6-chloro-2-{1-[2-(6-fluoro-1H-indol-3-yl)-ethyl]-piperidin-4-yl}-3H-quinazolin-4-one 70;
7-chloro-2-{1-[2-(6-fluoro-1H-indol-3-yl)-ethyl]-piperidin-4-yl}-3H-quinazolin-4-one 72;
5-fluoro-2-{1-[2-(6-fluoro-1H-indol-3-yl)-ethyl]-piperidin-4-yl}-3H-quinazolin-4-one 74;
6-fluoro-2-{1-[2-(6-fluoro-1H-indol-3-yl)-ethyl]-piperidin-4-yl}-3H-quinazolin-4-one 76;
7-fluoro-2-{1-[2-(6-fluoro-1H-indol-3-yl)-ethyl]-piperidin-4-yl}-3H-quinazolin-4-one 78;
6,7-difluoro-2-{1-[2-(6-fluoro-1H-indol-3-yl)-ethyl]-piperidin-4-yl}-3H-quinazolin-4-one 80;
6,7-dimethoxy-2-{1-[2-(6-fluoro-1H-indol-3-yl)-ethyl]-piperidin-4-yl}-3H-quinazolin-4-one 84; or
pharmaceutically acceptable salts, hydrates or N-oxides thereof Even more preferred compounds of Formula (I) include:
2-{1-[2-(1H-indol-3-yl)-ethyl]-piperidin-4-yl}-3H-quinazolin-4-one 10;
2-{1-[2-(6-fluoro-1H-indol-3-yl)-ethyl]-piperidin-4-yl}-3H-quinazolin-4-one 66;
7-fluoro-2-{1-[2-(6-fluoro-1H-indol-3-yl)-ethyl]-piperidin-4-yl}-3H-quinazolin-4-one 78
6-fluoro-2-{1-[2-(6-fluoro-1H-indol-3-yl)-ethyl]-piperidin-4-yl}-3H-quinazolin-4-one 76;
6,7-difluoro-2-{1-[2-(6-fluoro-1H-indol-3-yl)-ethyl]-piperidin-4-yl}-3H-quinazolin-4-one 80,
or pharmaceutically acceptable salts, hydrates or N-oxides thereof.

GENERAL SYNTHETIC REACTION SCHEME

Compounds of the present invention may be made by the methods depicted in the illustrative synthetic reaction scheme shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. The following synthetic reaction schemes are merely illustrative of some methods by which the compounds of the present invention may be synthesized, and various modifications to these synthetic reaction schemes may be made and will be suggested to one skilled in the art having referred to the disclosure contained in this Application.

The starting materials and the intermediates of the synthetic reaction schemes may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein preferably take place at atmospheric pressure over a temperature range from about −78° C. to about 150° C., more preferably from about 0° C. to about 125° C.

In general, the compounds of Formula I can be prepared by the process of the following Reaction Scheme.

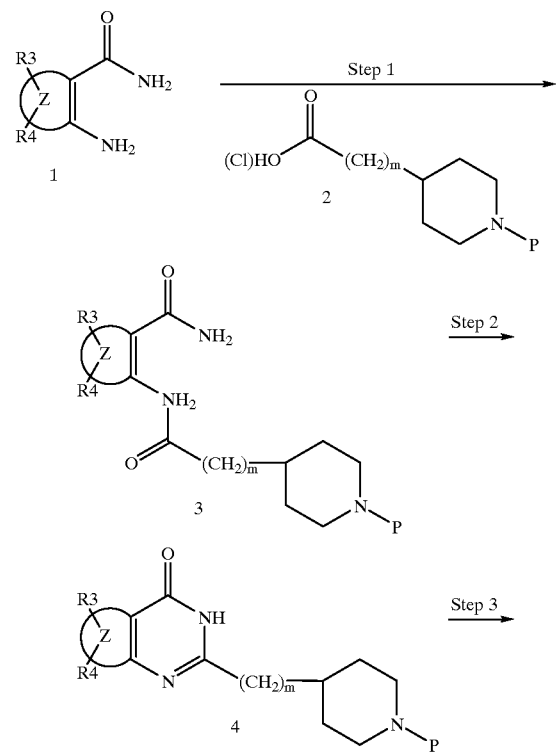

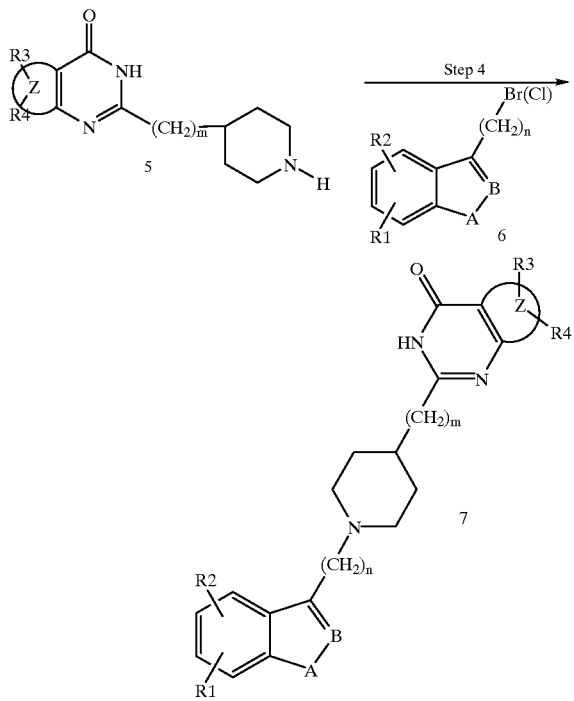

In step 1, an anthranilamide (2-aminobenzamide) (1, Z is benzene) or an amino-nicotinamide (1, Z is pyridine), can for example be condensed with an N-protected piperidine-4-carboxylic acid to afford product 3. Anthranilamides (1, Z is benzene) or amino-nicotimamides (1, Z is pyridine) are commercially available, or can be prepared from commercially available anthranilic acids (2-aminobenzoic acids) (Z is benzene) or amino-nicotinic acids (Z is pyridine) by conventional means such as conversion to the isatoic (Z is benzene) or azaisatoic (Z is pyridine) anhydride by treatment with phosgene in the presence of a base followed by treatment with ammonium hydroxide as described by Sellstedt et al., *J. Med. Chem.* 1975, 18, 926. Suitable N-protecting groups include acetyl, carbobenzyloxy (CBZ), and tert-butoxycarbonyl (BOC), preferably acetyl or and tert-butoxycarbonyl. The condensation can be performed in the presence of a carbodiimide coupling agent such as N,N-dicyclohexylcarbodiimide (DCC) or 1-(2-dimethylaminopropyl)-3-ethylcarbodiimide (EDC) in a suitable solvent such as chloroform, dichloromethane, dichloroethane, tetrahydrofuran, or pyridine at room temperature. Alternatively, the anthranilic amide (1, Z is benzene) or the amino-nicotinamide (1, Z is pyridine) can be reacted with an activated carboxylic acid derivative such as the acid chloride in a similar solvent in the presence of a base such as triethylamine. In this case the preferred protecting group P is acetyl. Standard mixed anhydride coupling can also be used to effect the condensation, e.g., treatment of the acid with a chloroformate, such as isobutyl chloroformate, in an aprotic solvent such as dichloromethane followed by addition of the anthranilic amide 1.

In step 2, benzamides (3, Z is benzene) or nicotinamides (3, Z is pyridine) can be converted to the N-protected 2-(piperidin-4-yl) quinazolinones (4, Z is benzene) or to the N-protected 2-(piperidin-4-yl) azaquinazolinones (4, Z is pyridine) by treatment with a strong base, such as potassium hydroxide, sodium hydride, sodium methoxide, or potassium tert-butoxide in a polar solvent. Suitable solvents may include ethanol, N,N-dimethylformamide, pyridine, or 2-methoxyethyl ether (diglyme). Preferable conditions can be treatment with sodium hydroxide in diglyme at 140° C. as described by Hori, et al., *Chem. Pharm. Bull.* 1991, 39, 367. Quinazolinones 4 can also be obtained from the corresponding acylated 2-aminobenzonitrile derivative by cyclization conditions well known in the literature (e.g., treatment with sodium hydroxide and hydrogen peroxide in aqueous ethanol as described in Jiang, et al., *J. Med. Chem.* 1990, 33, 1721.

In step 3, the protecting group P can be removed under standard conditions. When the protecting group is acetyl, removal can be affected by treatment with strong aqueous acid, such as hydrochloric acid, at 80–100° C. Removal of the BOC protecting group can be accomplished by treatment with trifluoroacetic acid in a chlorinated hydrocarbon solvent, such as dichloromethane or dichloroethane or by treatment with alcoholic mineral acid, such as hydrochloric acid in ethanol. The carbobenzyloxy protecting group can be removed with strong acid, such as hydrobromic acid in acetic acid, or by hydrogenolysis.

In step 4, for example, the 2-(piperidin-4-yl) quinazolinones (5, Z is benzene) or the 2-(piperidin-4-yl) azaquinazolinones (5, Z is pyridine) can be alkylated for example with a 3-(2-bromoethyl)indole (6, A—B is NH—C, n is 2) or a 3-(2-bromoethyl)indazole (6, A—B is NH—N, n is 2) to afford the final compounds 7. The alkylation reaction can be carried out in the presence of a base such as triethylamine or potassium carbonate in a suitable solvent such as tetrahydrofuran, ethanol, acetonitrile, N,N-dimethylformamide, dimethyl sulfoxide, or 1-methyl-2-pyrrolidinone at temperatures from 25–100° C. The 3-(2-bromoethyl)indoles (6, A—B is NH—C, n is 2) are commercially available or can be prepared in three steps from the corresponding indole by the procedure described by Neumeyer et al., *J. Med. Chem.* 1969, 12, 450 and references cited therein. The 3-(2-bromoethyl)indazoles (6, A—B is NH—N, n is 2) are similarly prepared from the corresponding 3-indazoleacetic acids which can be prepared by the method described by Mylari et al., *J. Med. Chem.* 1992, 35, 2155. Alternatively, 3-(2-chloroethyl)indole and 3-(2-chlorooethyl)indazole derivatives can be used in place of the bromo compounds 6.

General Utility

Alpha$_1$-adrenoceptors mediate the contractile state of smooth muscle tissue and are present in the human prostate, bladder neck and urethra. Alpha$_1$-adrenoceptor stimulation also produces contraction of urethral and bladder neck smooth muscle, leading to increased resistance in urinary outflow. Thus, alpha$_1$-adrenoceptor antagonists may be useful in preventing and treating disorders or symptoms related to uropathies, such as reduction or alleviation of urinary tract disorders, for example, overactive bladder, urinary frequency, nocturia, urinary urgency, detrusor hyperreflexia, outlet obstruction, BPH, prostatitis, urge incontinence, urethritis, idiopathic bladder hypersensitivity, and the like.

Alpha$_1$-adrenoceptor antagonists have been shown in numerous clinical studies to be effective in relieving the symptoms associated with benign prostatic hypertrophy (BPH). Drugs such as prazosin, indoramin, doxazosin and the newer compound tamsulosin are in common clinical use for BPH, and are effective in reducing both "obstructive" symptoms (e.g. low flow rate) and "irritative" symptoms (e.g. urinary urge and frequency, nocturia). However, these compounds are all non-subtype-selective, and have the potential to cause significant side-effects, particularly cardiovascular effects such as postural hypotension, and CNS effects including aesthenia (tiredness). These effects can limit dosing and thus clinical efficacy in reducing symptoms associated with BPH.

Pharmacological studies resulting in the subdivision of $alpha_1$-adrenoceptors into $alpha_{1A}$-, $alpha_{1B}$- and $alpha_{1D}$-adrenoceptors have led to the suggestion that development of subtype-selective antagonists may allow improved symptomatic treatment of BPH/unstable bladder with a lower incidence of dose-limiting side-effects. Recently, much interest has focused on the role of the $alpha_{1A}$-adrenoceptor subtype in BPH, as a result of studies demonstrating that this subtype predominates in the urethra and prostate of man (Price et al., 1993; Faure et al, 1994; Taniguchi et al., 1997), and appears to be the receptor mediating NA-induced smooth muscle contraction in these tissues (Forray et al., 1994; Hatano et al., 1994; Marshall et al., 1995). The resulting tone is believed to contribute substantially to the total urinary outflow obstruction observed in patients with BPH (Furuya et al., 1982), with the remaining being attributable to increased prostate mass. These observations have fueled the hypothesis that an $alpha_{1A}$-subtype-selective antagonist may, via a selective and significant decrease in outlet resistance, lead to improved pharmacotherapy for BPH.

$Alpha_{1B}$-adrenoceptors are present in the liver, heart and cerebral cortex and are believed to be involved in mediating vascular contractile and blood pressure responses. $Alpha_{1B}$-adrenoceptors are also present in areas of the spinal cord which receive input from sympathetic neurons originating in the pontine micturition center and are presumed to be involved in the regulation of bladder function. Additionally, $alpha_{1B}$-adrenoceptor antagonists are useful as analgesic/antihyperalgesic therapies for treating pain, including symptoms of acute pain, inflammatory pain, neuropathic pain (including thermal and mechanical hyperalgesia as well as thermal and mechanical allodynia), complex regional pain syndromes (including reflex sympathetic dystrophy, causalgia and sympathetically maintained pain and the like.

However, it must be noted that in BPH, it is often the irritative symptoms which prompt the patient to seek treatment, and that these irritative symptoms may be present even in patients with no demonstrable obstruction (i.e. normal urine flow rates). By combining both $alpha_{1A}$- and $alpha_{1B}$-subtype-selectivity in a compound, a reduction of both obstructive and irritative symptoms in patients with BPH may be achieved. Lower levels or lack of $alpha_{1D}$-adrenoceptor antagonism should lead to reduced or fewer side effects than those associated with the use of non-subtype-selective agents.

In a preferred embodiment, the compounds of this invention are useful for treating disorders and symptoms which can be ameliorated by blockade of $alpha_1$-adrenoceptors, such as reduction or alleviation of urinary tract disorders, for example, pelvic hypersensitivity (including interstitial cystitis, prostatitis, pelvic pain syndrome, infectious cystitis, prostatodynia, and the like), overactive bladder, urinary frequency, nocturia, urinary urgency, detrusor hyperreflexia, outlet obstruction, BPH, prostatitis, urge incontinence, urethritis, idiophatic bladder hypersensitivity, and the like.

In another preferred embodiment, the compounds of this invention are useful for treating disorders and symptoms which can be ameliorated by blockade of $alpha_1$-adrenoceptors, such as reduction or alleviation of pain disorders, for example inflammatory pain, neuropathic pain, cancer pain, acute pain, chronic pain or complex regional syndromes.

In a more preferred embodiment, the compounds of this invention are useful for treating disorders and symptoms which can be ameliorated by blockade of both $alpha_{1A}$- and $alpha_{1B}$-adrenoceptors with lower to no blockade of $alpha_{1D}$-adrenoceptor, such as reduction or alleviation of both outlet obstruction, such as benign prostatic hypertrophy, and irritative symptoms, such as pain.

These and other therapeutic uses are described, for example, in Goodman & Gilman's, The Pharmacological Basis of Therapeutics, ninth edition, McGraw-Hill, New York, 1996, Chapter 26:601–616; and Coleman, R. A., Pharmacological Reviews, 1994, 46:205–229.

Testing

The pharmacology of the compounds of this invention was determined by art recognized procedures. The in vitro techniques for determining the affinities of test compounds at $alpha_1$-adrenoceptor subtypes in radioligand binding and functional assays are described in Example 16.

The effect of the compounds of this invention on blood pressure can be evaluated by any method known in the art. Examples of such methods are the Rat In Vivo, Blood Pressure Assay; the Rat in Vivo, Tilt-Response Assay; and the Dog, In Vivo, Blood and Intraurethral Pressure assay. An in vivo assay for measuring the blood pressure lowering effects of test compounds in normotensive rats is described in Example 17. An in vivo assay for measuring the relative effect of a test compound on hypogastric nerve stimulation-induced increases in intraurethral pressure and phenylephrine-induced increases in diastolic blood pressure in anesthetized dog is described in Example 20.

The analgesic activity of the compounds of this invention can be evaluated by any method known in the art. Examples of such methods are the Tail-flick test (D'Amour et al. (1941) J. Pharmacol. Exp. and Ther. 72:74–79); the Rat Tail Immersion Model, the Carrageenan-induced Paw Hyperalgesia Model, the Formalin Behaavioral Response Model (Dubuisson et al., Pain, 1977, 4:161–174), the Von Frey Filament Test (Kim et al., Pain, 1992, 50:355–363), the Chronic Constriction Injury, the Radian Heat Model, and the Cold Allodynia Model (Gogas et al., Analgesia, 1997, 3:111–118) An in vivo assay for measuring the effect of test compounds on the pain response to radiant heat in neuropathic rats is described in Example 18. An in vivo assay for measuring the effect of test compound on the cold allodynia response in neuropathic rats is described in Example 19.

The potential of $alpha_1$-adrenoceptor antagonists to cause postural hypotension can be evaluated for example with the blood withdrawal model in conscious rat. An in vivo assay for measuring the effect of test compounds on postural hypotension in conscious rats is described in Example 21.

Preferred compounds of this invention generally demonstrate selectivity for the $alpha_{1A/B}$-subtype over the $alpha_{1D}$-subtype. The compounds of this invention may reduce both obstructive and irritative symptoms in patients with BPH. The lack of $alpha_{1D}$-adrenoceptor antagonism is expected to lead to reduced or fewer side effects than those associated with the use of non-subtype-selective agents.

Administration and Pharmaceutical Composition

The present invention includes pharmaceutical compositions comprising a compound or compounds of the present invention or a pharmaceutically acceptable salt, hydrate, N-oxide or other derivative thereof together with one or more pharmaceutically acceptable carriers, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), (for example, dichlorodifluoromethane, trichlorofluoromethane, or dichlorotetrafluoroethane), carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa. Representative pharmaceutical formulations containing a compound of the present invention are described in Examples 9–15.

EXAMPLES

The following preparations and examples are given to enable those skilled in the art to more clearly understand and practice the present invention. They should mot be considered as limiting the scope of the invention, but merely as being illustrative and representative thereof.

Example 1

4-(2-Carbamoyl-phenylcarbamoyl)-piperidine-1-carboxylic acid tert-butyl ester (3, $R_3$, $R_4$=H, P=BOC, m=0, Z=benzene)

A solution of 2-aminobenzoic acid (about 2.7 g, 20 mmol), N-(tert-butoxycarbonyl) -4-piperidinecarboxylic acid (about 4.5 g, 20 mmol) and 1-[3-(dimethylamino) propyl]-3-ethylcarbodiimide hydrochloride (EDC) (about 3.8 g, 20 mmol) in pyridine (about 25 mL) was stirred at room temperature for 18 h. The mixture was diluted with water, extracted twice with ethyl acetate, and the combined ethyl acetate extract was washed with water, dilute aqueous HCl, and brine, dried ($Na_2SO_4$) and evaporated in vacuo. The residue was crystallized from ether/hexane to afford compound 3 ($R_3$=H, P=BOC, m=0, Z=benzene) as a white solid (about 6.2 g, 91%); m.p. 153–154° C.

Example 2

2-[1-(tert-Butoxycarbonyl)-piperidin-4-yl]-3H-quinazolin-4-one (4, $R_3$, $R_4$=H, P=BOC, m=0, Z=benzene)

A mixture of compound 3 ($R_3$ $R_4$=H, P=BOC, m=0, Z=benzene) (about 3.5 g, 10 mmol) and potassium hydroxide (about 0.6 g, 10 mmol) in digylyme (20 mL) was stirred at 140° C. for 1.5 h. The cooled mixture was diluted with water, cooled in an ice bath, and neutralized with HCl. The precipitate was collected by filtration and washed with water to afford compound 4 ($R_3$, $R_4$=H, P=BOC, m=0, Z=benzene) (about 2.8 g, 85%) as a white solid; m.p. 225–227° C.

Example 3

2-(Piperidin-4-yl)-3H-quinazolin-4-one (5, $R_3$=H, m=0, Z=benzene)

Compound 4 ($R_3$ $R_4$=H, P=BOC, m=0, Z=benzene) (about 3.3 g, 10 mmol) was suspended in dichloromethane (10 mL) and trifluoroacetic acid (10 mL) was added. The resulting solution was stirred at room temperature for 30 min and then concentrated in vacuo. The residue was dissolved in water and solution was neutralized with ammonium hydroxide. The precipitate was filtered, washed with water and dried to afford the title compound as a white solid (about 2.1 g, 92%); m.p. 244–245° C.

The following were similarly prepared:

5-chloro-2-(piperidin-4-yl)-3H-quinazolin-4-one (5, $R_3$=5-Cl, $R_4$=H, m=0, Z=benzene); m.p. 259–260 C;

6-chloro-2-(piperidin-4-yl)-3H-quinazolin-4-one (5, $R_3$=6-Cl, $R_4$=H, m=0, Z=benzene); m.p. 253–255 C;

7-chloro-2-(piperidin-4-yl)-3H-quinazolin-4-one (5, $R_3$=7-Cl, $R_4$=H, m=0, Z=benzene); m.p. 248–249 C;

5-fluoro-2-(piperidin-4-yl)-3H-quinazolin-4-one (5, $R_3$=5-F, $R_4$=H, m=0, Z=benzene); m.p. 295–300 C;

6-fluoro-2-(piperidin-4-yl)-3H-quinazolin-4-one (5, $R_3$=6-F, $R_4$=H, m=0, Z=benzene); m.p. 247–248 C;

7-fluoro-2-(piperidin-4-yl)-3H-quinazolin-4-one (5, $R_3$=7-F, $R_4$=H, m=0, Z=benzene); m.p. 243–245 C;

6,7-difluoro-2-(piperidin-4-yl)-3H-quinazolin-4-one (5, $R_3$=6-F, $R_4$=7-F, m=0, Z=benzene); m.p. 250–252 C;

6-methoxy-2-(piperidin-4-yl)-3H-quinazolin-4-one (5, $R_3$=6-OMe, $R_4$=H, m=0, Z=benzene); m.p. 252–253° C.; and 6,7-dimethoxy-2-(piperidin-4-yl)-3H-quinazolin-4-one (5, $R_3$=6-OMe, $R_4$=7-OMe, m=0, Z=benzene); m.p. 254–256° C.

Example 4

2-{1-[2-(1H-Indol-3-yl)-ethyl]-piperidin-4-yl}-3H-quinazolin-4-one 10

A mixture of compound 5 ($R_3$, $R_4$=H, m=0, Z=benzene) (about 0.8 g, 3.5 mmol), 3-(2-bromoethyl)indole (6, $R_1$, $R_2$=H, A—B=NH—C, n=2) (about 0.8 g, 3.5 mmol) and triethylamine (about 0.7 mL, 5 mmol) in N,N-dimethylformamide (10 mL) was stirred at 80° C. for 2 h. The mixture was diluted with water and extracted with ethyl acetate. The ethyl acetate extract was washed with water (2×) and brine, dried ($Na_2SO_4$), and evaporated to afford a solid residue. Trituration with ether afforded the title compound 10 as a white solid (about 0.5 g, 38%). The dihydrochloride salt was crystallized from ethanol-ether; m.p. 268–270° C. Analysis for $C_{23}H_{24}N_4O \cdot 2HCl$: C, 62.02; H, 5.88; N, 12.51. Found: C, 61.79; H, 5.93; N, 12.51.

Alternatively, purification was effected by High Performance Liquid Chromatography (HPLC) and the title compound was isolated as the trifluoroacetate salt after evaporation of the acetonitrile-aqueous trifluoroacetic acid eluent in vacuo. Characterization was by electrospray ionization mass spectrometry (eims); $(M+1)^+=373$.

The following compounds were similarly prepared from quinazolinones 5 (m=0, Z=benzene) and 3-(2-bromoethyl) indole 6 (A—B=NH—C, n=2):

5-chloro-2-{1-[2-(1H-indol-3-yl)-ethyl]-piperidin-4-yl}-3H-quinazolin-4-one trifluoroacetate;12 eims: $(M+1)^+=407$;

6-chloro-2-{1-[2-(1H-indol-3-yl)-ethyl]-piperidin-4-yl}-3H-quinazolin-4-one trifluoroacetate;14 eims: $(M+1)^+=407$;

7-chloro-2-{1-[2-(1H-indol-3-yl)-ethyl]-piperidin-4-yl}-3H-quinazolin-4-one dihydrochloride;16 m.p. 190–195° C.;

5-fluoro-2-{1-[2-(1H-indol-3-yl)-ethyl]-piperidin-4-yl}-3H-quinazolin-4-one trifluoroacetate;18 eims: $(M+1)^+=392$;

6-fluoro-2-{1-[2-(1H-indol-3-yl)-ethyl]-piperidin-4-yl}-3H-quinazolin-4-one trifluoroacetate;20 eims: $(M+1)^+=392$;

7-fluoro-2-{1-[2-(1H-indol-3-yl)-ethyl]-piperidin-4-yl}-3H-quinazolin-4-one hydrochloride;22 m.p. 220–225° C.; and 6,7-difluoro-2-{1-[2-(1H-indol-3-yl)-ethyl]-piperidin-4-yl}-3H-quinazolin-4-one trifluoroacetate;24 eims: $(M+1)^+=425$.

The following compounds were similarly prepared from quinazolinones 5 (Z=benzene) and 3-(2-bromoethyl)-5-chloroindole (6, $R_1$=5-Cl, A—B=NH—C, n=2):

2-{1-[2-(5-chloro-1H-indol-3-yl)-ethyl]-piperidin-4-yl}-3H-quinazolin-4-one trifluoroacetate; 26 eims: $(M+1)^+=407$;

5-chloro-2-{1-[2-(5-chloro-1H-indol-3-yl)-ethyl]-piperidin-4-yl}-3H-quinazolin-4-one trifluoroacetate;28 eims: $(M+1)^+=441$;

6-chloro-2-{1-[2-(5-chloro-1H-indol-3-yl)-ethyl]-piperidin-4-yl}-3H-quinazolin-4-one trifluoroacetate;30 eims: $(M+1)^+=441$;

7-chloro-2-{1-[2-(5-chloro-1H-indol-3-yl)-ethyl]-piperidin-4-yl}-3H-quinazolin-4-one trifluoroacetate; 32 eims: $(M+1)^+=441$;

2-{1-[2-(5-chloro-1H-indol-3-yl)-ethyl]-piperidin-4-yl}-5-fluoro-3H-quinazolin-4-one trifluoroacetate; 34 eims: $(M+1)^+=425$;

2-{1-[2-(5-chloro-1H-indol-3-yl)-ethyl]-piperidin-4-yl}-6-fluoro-3H-quinazolin-4-one trifluoroacetate; 36 eims: $(M+1)^+=425$;

2-{1-[2-(5-chloro-1H-indol-3-yi)-ethyl]-piperidin-4-yl}-7-fluoro-3H-quinazolin-4-one trifluoroacetate; 38 eims: $(M+1)^+=425$; and 2-{1-[2-(5-chloro-1H-indol-3-yl)-ethyl]-piperidin-4-yl}-6,7-difluoro-3H-quinazolin-4-one trifluoroacetate; 40 eims: $(M+1)^+=443$.

The following compounds were similarly prepared from quinazolinones 5 (m=0, Z=benzene) and 3-(2-bromoethyl)-6-chloroindole (6, $R_1$=6-Cl, A—B =NH—C, n=2):

2-{1-[2-(6-chloro-1H-indol-3-yl)-ethyl]-piperidin-4-yl}-3H-quinazolin-4-one trifluoroacetate; 42 eims: $(M+1)^+=407$;

5-chloro-2-{1-[2-(6-chloro-1H-indol-3-yl)-ethyl]-piperidin-4-yl}-3H-quinazolin-4-one trifluoroacetate; 44 eims: $(M+1)^+=441$;

6-chloro-2-{1-[2-(6-chloro-1H-indol-3-yl)-ethyl]-piperidin-4-yl}-3H-quinazolin-4-one trifluoroacetate; 46 eims: $(M+1)^+=441$;

7-chloro-2-{1-[2-(6-chloro-1H-indol-3-yl)-ethyl]-piperidin-4-yl}-3H-quinazolin-4-one trifluoroacetate; 48 eims: $(M+1)^+=441$;

2-{1-[2-(6-chloro-1H-indol-3-yl)-ethyl]-piperidin-4-yl}-5-fluoro-3H-quinazolin-4-one trifluoroacetate; 50 eims: $(M+1)^+=425$;

2-{1-[2-(6-chloro-1H-indol-3-yl)-ethyl]-piperidin-4-yl}-6-fluoro-3H-quinazolin-4-one trifluoroacetate; 52 eims: $(M+1)^+=425$;

2-{1-[2-(6-chloro-1H-indol-3-yl)-ethyl]-piperidin-4-yl}-7-fluoro-3H-quinazolin-4-one trifluoroacetate; 54 eims: $(M+1)^+=425$; and 2-{1-[2-(6-chloro-1H-indol-3-yl)-ethyl]-piperidin-4-yl}-6,7-difluoro-3H-quinazolin-4-one trifluoroacetate; 56 eims: $(M+1)^+=443$.

The following compounds were similarly prepared from quinazolinones 5, (m=0, Z=benzene) and 3-(2-bromoethyl)-5-fluoroindole (6, $R_1$=5-F, A—B=NH—C, n=2):

2-{1-[2-(5-fluoro-1H-indol-3-yl)-ethyl]-piperidin-4-yl}-3H-quinazolin-4-one hydrochloride; 58 m.p. 298–301° C.;

6-chloro-2-{1-[2-(5-fluoro-1H-indol-3-yl)-ethyl]-piperidin-4-yl}-3H-quinazolin-4-one hydrochloride; 60 m.p. 290° C. (dec);

7-chloro-2-{1-[2-(5-fluoro-1H-indol-3-yl)-ethyl]-piperidin-4-yl}-3H-quinazolin-4-one hydrochloride; 62 m.p. 300° C. (dec); and 7-fluoro-2-{1-[2-(5-fluoro-1H-indol-3-yl)-ethyl]-piperidin-4-yl}-3H-quinazolin-4-one hydrochloride; 64 m.p. 283° C. (dec).

The following compounds were similarly prepared from quinazolinones 5 (m=0, Z=benzene) and 3-(2-bromoethyl)-6-fluoroindole (6, $R_1$=6-F, A—B =NH—C, n=2):

2-{1-[2-(6-fluoro-1H-indol-3-yl)-ethyl]-piperidin-4-yl}-3H-quinazolin-4-one hydrochloride; 66 m.p. 263–264° C.;

5-chloro-2-{1-[2-(6-fluoro-1H-indol-3-yl)-ethyl]-piperidin-4-yl}-3H-quinazolin-4-one trifluoroacetate; 68 eims: $(M+1)^+=425$;

6-chloro-2-{1-[2-(6-fluoro-1H-indol-3-yl)-ethyl]-piperidin-4-yl}-3H-quinazolin-4-one hydrochloride; 70 m.p. 292–294° C.;

7-chloro-2-{1-[2-(6-fluoro-1H-indol-3-yl)-ethyl]-piperidin-4-yl}-3H-quinazolin-4-one hydrochloride; 72 m.p. 256–266° C.;

5-fluoro-2-{1-[2-(6-fluoro-1H-indol-3-yl)-ethyl]-piperidin-4-yl}-3H-quinazolin-4-one trifluoroacetate;74 eims: $(M+1)^+=409$;

6-fluoro-2-{1-[2-(6-fluoro-1H-indol-3-yl)-ethyl]-piperidin-4-yl}-3H-quinazolin-4-one dihydrochloride; 76 m.p. 195–197° C.;

7-fluoro-2-{1-[2-(6-fluoro-1H-indol-3-yl)-ethyl]-piperidin-4-yl}-3H-quinazolin-4-one hydrochloride; 78 m.p. 205–209° C.;

6,7-difluoro-2-{1-[2-(6-fluoro-1H-indol-3-yl)-ethyl]-piperidin-4-yl}-3H-quinazolin-4-one dihydrochloride; 80 m.p. 215–217° C.;

2-{1-[2-(6-fluoro-1H-indol-3-yl)-ethyl]-piperidin-4-yl}-6-methoxy-3H-quinazolin-4-one hydrochloride; 82 m.p. 230–232° C.; and 2-{1-[2-(6-fluoro-1H-indol-3-yl)-ethyl]-piperidin-4-yl}-6,7-dimethoxy-3H-quinazolin-4-one hydrochloride; 84 m.p. 229–231° C.

The following compounds were similarly prepared from quinazolinones 5 (m=0, Z=benzene) and 3-(2-bromoethyl)-5-chloro-1H-indazole (6, $R_1$=5-Cl, n=2, A—B =NH—N):

2-{1-[2-(5-chloro-1H-indazol-3-yl)-ethyl]-piperidin-4-yl}-3H-quinazolin-4-one trifluoroacetate;86 eims: $(M+1)^+$=408;

5-chloro-2-{1-[2-(5-chloro-1H-indazol-3-yl)-ethyl]-piperidin-4-yl}-3H-quinazolin-4-one trifluoroacetate; 88 eims: $(M+1)^+$=442;

6-chloro-2-{1-[2-(5-chloro-1H-indazol-3-yl)-ethyl]-piperidin-4-yl}-3H-quinazolin-4-one trifluoroacetate; 90 eims: $(M+1)^+$=442;

7-chloro-2-{1-[2-(5-chloro-1H-indazol-3-yl)-ethyl]-piperidin-4-yl}-3H-quinazolin-4-one trifluoroacetate, 92 eims: $(M+1)^+$=442;

2-{1-[2-(5-chloro-1H-indazol-3-yl)-ethyl]-piperidin-4-yl}-5-fluoro-3H-quinazolin-4-one trifluoroacetate; 94 eims: $(M+1)^+$=426;

2-{1-[2-(5-chloro-1H-indazol-3-yl)-ethyl]-piperidin-4-yl}-6-fluoro-3H-quinazolin-4-one trifluoroacetate; 96 eims: $(M+1)^+$=426;

2-{1-[2-(5-chloro-1H-indazol-3-yl)-ethyl]-piperidin-4-yl}-7-fluoro-3H-quinazolin-4-one trifluoroacetate; 98 eims: $(M+1)^+$=426; and 2-{1-[2-(5-chloro-1H-indazol-3-yl)-ethyl]-piperidin-4-yl}-6,7-difluoro-3H-quinazolin-4-one trifluoroacetate; 100 eims: $(M+1)^+$=444.

The following compound was similarly prepared from quinazolinone 5 ($R_3$=H, m=0, Z=benzene) and 3-(2-bromoethyl)-6-fluoro-1H-indazole (6, $R_1$=6-F, n=2, A—B =NH—N):

2-{1-[2-(6-fluoro-1H-indazol-3-yl)-ethyl]-piperidin-4-yl}-3H-quinazolin-4-one trifluoroacetate; 102 eims: $(M+1)^+$=392.

Example 5

4-(3-Carbamoyl-pyridin-2-ylcarbamoyl)-piperidine-1-carboxylic acid tert-butyl ester (3, $R_3R_4$=H, P=BOC, m=0, Z=pyridine)

A solution of 2-amino-nicotineamide amide (about 179 mg, 1.3 mmol), N-(tert-butoxycarbonyl)-4-piperidinecarboxylic acid (about 450 mg, 1.96 mmol) and 1-[3-(dimethylamino)propyl]-3-ethylcarbodiimide hydrochloride (EDC) (about 385 mg, 2.0 mmol) in pyridine (7.5 mL) was stirred at room temperature for 18 h. Sat. NaHCO$_3$ (25 ml) was added to the obtained yellow solution, and the mixture was extracted with ethyl acetate. The organic layers were washed with brine, dried (MgSO$_4$) and evaporated in vacuo. The residue was crystallized from acetone/hexane to afford compound 3 ($R_3$=H, P=BOC, m=0, Z=pyridine) as a white solid (about 266 mg, 58%).

Example 6

8-Aza-2-[1-(tert-butoxycarbonyl)-piperidin-4-yl]-3H-quinazolin-4-one (4, $R_3$, $R_4$=H, P=BOC, m=0, Z=pyridine)

A mixture of compound 3 ($R_3$, $R_4$=H, P=BOC, m=0, Z=pyridine) (about 937 mg, 2.69 mmol) and potassium hydroxide (about 178 mg, 3.17 mmol) in digylyme (15 mL) was stirred at 140° C. for 1 h. The cooled mixture was diluted with water, cooled in an ice bath, and neutralized with 1M HCl and sat. NaHCO$_3$ (100 ml). The mixture was extracted with ethyl acetate. The organic layers were washed with brine, combined, dried (MgSO$_4$) and concentrated to afford compound 4 ($R_3$, $R_4$=H, P=BOC, m=0, Z=pyridine) (about 866 mg, 97%) as a white solid.

Example 7

8-Aza-2-(piperidin-4-yl)-3H-quinazolin-4-one (5, $R_3$=H, m=0, Z=pyridine)

Compound 4 ($R_3$, $R_4$=H, P=BOC, m=0, Z=pyridine) (about 543 mg, 1.64 mmol) was suspended in dichloromethane (5 mL) and trifluoroacetic acid was added. The resulting solution was stirred at room temperature for 30 min and then concentrated in vacuo. The residue was dissolved in methanol (5 ml) and precipitated from ether (150 ml). The precipitate was filtered, washed with water and dried to afford the title compound as a white solid (about 542 mg, 87%).

Example 8

8-Aza-2-{1-[2-(6-fluoro-1H-indol-3-yl)-ethyl]-piperidin-4-yl}-3H-quinazolin-4-one 104

A mixture of compound 5 ($R_3$, $R_4$=H, m=0, Z=pyridine) (about 112 mg, 296 pmol), 3-(2-bromoethyl)-6-fluoroindole (6, $R_1$=6-F, $R_2$=H, A—B=NH—C, n=2) (about 64 mg, 264 pmol) and triethylamine (about 200 µL, 1.43 mmol) in N,N-dimethylformamide (2 mL) was stirred at 80° C. for 2.5 h. After cooling to room temperature, sat. NaHCO$_3$. (25 ml) was added. The mixture was diluted with water and extracted with ethyl acetate. The ethyl acetate extract was washed with water (2×) and brine, dried (MgSO$_4$), and evaporated to afford a solid residue. Chromatography afforded the title compound 104 as a white solid. The obtained white solid was suspended in 2 ml 10% HCl in EtOH. After addition of ether (20 ml) the precipitate of the trihydrochloride salt was filtered off yielding a yellow solid (about 48 mg, 35%). Analysis for $C_{17}H_{22}N_4O_3$.3.3HCl: C, 51.63; H, 4.98; N, 13.68. Found: C, 51.50; H, 5.14; N, 13.48.

Example 9

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Example 10

Composition for Oral Administration

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Example 11

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Example 12

Parenteral Formulation (IV)

| Ingredient | % wt./wt. |
| --- | --- |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Example 13

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example 14

Topical Formulation

| Ingredients | grams |
| --- | --- |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Example 15

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 16

[$^3$H]prazosin Binding (alpha$_1$-Adrenoceptor) Assay

Alpha$_{1A}$, alpha$_{1B}$, and alpha$_{1D}$ adrenoceptor transfected CHO-K1 cells, prepared using the methods described in Chang et al. (1998) FEBS Lett. 422:279–283, were grown to confluence in T-162 tissue culture flasks in Ham's F-12 culture medium supplemented with 10% fetal bovine serum, geneticin (150 $\mu$g/mL) and streptomycin/penicillin (30 $\mu$g/mL/30 $\mu$g/mL) at 37° C. in 7% $CO_2$. Cells were harvested by incubating with phosphate-buffered saline (PBS) containing 30 $\mu$M EDTA for 5–10 min at 37° C. Cells were pelleted by centrifuging at 500×g for 5 min, the pelleted cells are homogenized (Polytron homogenizer) in 10 vols (w/v) of 50 mM Tris, 1 mM EDTA, (homogenisation buffer, pH 7.4 at 4° C.). The homogenate was centrifuged at 45,000×g for 20 min. The pellet was resuspended in the homogenizing buffer and rehomogenized. The resulting homogenate was centrifuged at 45,000×g for 20 min. The pellet was resuspended in 50 mM Tris buffer (pH 7.4 at 4° C.), aliquoted, frozen, and stored at −80° C. for further use.

The membranes were thawed at room temperature and diluted in assay buffer (50 mM Tris buffer at pH 4) at 37° C. and homogenized using the Polytron tissue disrupter. The membranes were incubated with the radioligand ([$^3$H] prazosin, NEN, 0.1–0.5 nM) and test compound at 37° C. for 30 min. The membranes were then filtered over polyethyleneimine-treated GF/B unifilter plates using a Packard Filtermate Harvester and washed with ice-cold 50 mM Tris-HCl, 1 mM EDTA buffer (3×3 sec. washes). Scintillation cocktail was added to the filter plates and bound radioligand determined by liquid scintillation spectrophotometry.

For each experiment, total binding (in the absence of any test or reference compounds) and non-specific binding (10 $\mu$M phentolamine) were determined. For each sample tested, the concentration producing 50% inhibition of binding (IC$_{50}$) and Hill Slope (n$_H$) was determined using iterative non-linear curve fitting techniques with Kaleidagraph (Synergy Software) or other appropriate software. If the radioligand $K_D$ was known, the inhibition dissociation constant ($K_i$) of each ligand was determined according to the method of Cheng and Prusoff (Cheng, Y-C. and Prusoff, W. H., Biochem. Pharmacol., (1973), 22:3099–3108).

Proceeding as in Example 16, compounds of Formula (I) were tested and found to be selective $alpha_{1A/B}$-adrenoceptor antagonists.

Example 17

Rat In Vivo, Blood Pressure Assay

The following describes an in vivo assay for measuring the effect of test compounds on blood pressure in normotensive and spontaneously hypertensive rats.

Normotensive or spontaneously hypertensive rats (0.25 to 0.45 kg) were fasted for 18 h and anesthetized with ether. The right femoral vein was isolated and cannulated with a fluid filled polyethylene cannulae for bolus administration of test substances. The right femoral artery was isolated and cannulated with a fluid filled polyethylene cannula connected to an external pressure transducer for monitoring mean arterial blood pressure (MAP).

Following cannulation, rats were pretreated (intravenous route) with an angiotensin receptor antagonist, a beta-adrenergic receptor antagonist and an $alpha_2$ adrenergic receptor antagonist as described in Blue et al. (*Br. J. Pharmacol.* 120:107P, 1997).

The rats were placed in restrainers and allowed to recover from anesthesia. Following a 30–60 minute period for stabilization, the test compounds or vehicles were administered intravenously. Following the last dose of test compound, prazosin was optionally administered, i.v., to determine hypotensive effects obtained by non-subtype-selective blockade of $alpha_1$-adrenoceptors. Blood pressure and heart rate are monitored continuously for at least 4 hrs. post-administration.

Proceeding as in Example 17, compounds of Formula (I) were tested and found to be considerably less potent than prazosin at producing blood pressure lowering effects.

Example 18

Pain Response to Radiant Heat in Neuropathic Rats

The following describes an in vivo assay for measuring the effect of test compounds on the pain response to radiant heat in neuropathic rats.

Male Sprague-Dawley rats (Harlan, 240–300 g) are surgically prepared to have a chronic constriction injury (CCI) as described above 13–15 days prior to testing. Rats are selected for the study according to the following criteria: ligated leg ($L_L$)latency −4 to 14 seconds; sham leg ($L_S$) latency −6 to 18 seconds; difference ($L_{Diff}=L_L-L_S$)-greater than 1.5 seconds. Selected rats are randomly assigned to treatment groups and dosed at 0 (vehicle, 10 mL/kg, 0.5% CMC, 30, 60, 100 or 300 µg/kg, ip. After 1 hour post-dosing, rats are placed under inverted plastic cages on an elevated glass platform. For each rat, four trials of each of the following are performed: shone light on the left hind paw (sham) and recorded the latency when the paw is withdrawn; shone light on the right hind paw (ligated) and recorded the latency when the paw is withdrawn. Five minute intervals are allowed between trials. Hind paws are examined for redness and blistering after each test.

Proceeding as in Example 18, compounds of Formula (I) are tested and assayed for a significant effect in the radiant heat assay.

Example 19

Cold Allodynia Response in Neuropathic Rats

The following describes an in vivo assay for measuring the effect of test compounds on the cold allodynia response in neuropathic rats.

Male Sprague-Dawley rats (Harlan, 160–200 g) were surgically prepared to have a chronic constriction injury (CCI) as described above 6 days prior to testing. Rats were selected for the study according to the following criteria: 1) the average of two trials was less than or equal to 13 sec; and 2) there was consistency across the two trial scores. Animals were screened for hypersensitivity to cold on post-surgery days 4 through 10, and selected for inclusion in dose-response studies based on the criteria described above. The pre-dose screening values were used as the animals' baseline cold allodynia scores.

Selected rats were tested twice in the cold bath assay described above for a pre-dose baseline and randomly assigned to treatment groups and dosed at 0 (vehicle, 10 mL/kg, 0.5% CMC, 30, 100 or 300 µg/kg, ip. After 1 hour and 3 hours post-dosing, rats were tested in the cold bath assay. For each rat, the assay was run once at 1 and 3 hours post-dose. The time to raise the rear leg was recorded in each trial. The maximal observing time in each trial was 20 seconds.

Proceeding as in Example 19, compounds of Formula (I) were tested and assayed for a significant effect in the cold allodynia response assay.

Example 20

Dog In Vivo, Blood and Intraurethral Pressure Assay

The following describes an in vivo assay for measuring the relative effect of test compounds on hypogastric nerve stimulation-induced increases in intraurethral pressure and phenylephrine-induced increases in diastolic blood pressure in anesthetized dog.

Mongrel dogs (10 to 20 kg) were fasted for 12 to 18 hours and anesthetized with phenobarbital sodium (35 mg/kg, i.v.). An endotracheal tube was inserted and thereafter the lungs were mechanically ventilated with room air. The right femoral vein was isolated and cannulated with two polyethylene cannulae, one for the administration of a continuous infusion of phenobarbital sodium (5 to 10 mg/kg/hr) and the other for bolus administration of test substances. The right femoral artery was isolated and cannulated to the abdominal aorta with a fluid filled polyethylene cannula connected to an external pressure transducer for monitoring diastolic aortic pressure (DAP). The bladder was exposed via a ventral midline abdominal incision and emptied of urine through a 22 gauge needle. The bladder was cannulated through a stab incision with a water filled balloon catheter connected to an external pressure transducer for monitoring prostatic intraurethral pressure (IUP). The right hypogastric nerve (HGN) was carefully isolated and attached to a Dastre's electrode for nerve stimulation.

The preparation was allowed to stabilize for at least 30 minutes and must have had a stable basal IUP for not less than 15 minutes prior to commencement or the assay protocol. The HGN was stimulated (20–50V, 10 Hz, 10 msec pulse train for 10 sec) to induce a measurable increase in IUP and then phenylephrine (PE) was administered by bolus injection (0.5 to 0.6 µg/kg, i.v.) to induce a measurable increase in DUP. The HGN stimulation and PE bolus injection were repeated every 5 minutes until three consecutive reproducible increases in IUP and DAP were achieved. Vehicle (0.1 to 0.3 mL/kg) was administered and 20 minutes later the HGN stimulation and PE bolus injection were repeated. Test compound was then administered and 20 minutes later the HGN stimulation and PE bolus injection were repeated. Test compound is administered approximately every 20 minutes, increasing the dose until maximal or near maximal inhibition of the increases in IUP and DAP is attained.

Proceeding as in Example 20, compounds of Formula (I) were tested and found to selectively inhibit the HGN stimulation-induced increases in IUP. In contrast, prazosin inhibited increases in IUP and DAP in similar fashion.

Example 21

Blood Withdrawal Model in Conscious Rat

Short-term maintenance of blood pressure during postural changes, such as on standing—when venous return to the heart is compromised by blood pooling in the lower extremities—is critically dependent on sympathetic vasoconstriction, mediated via alpha1-adrenoceptors. Since clinical use of non-subtype selective alpha1-adrenoceptor antagonists is known to be associated with significant incidence of postural hypotension, this model, in which venous pooling has been mimicked by blood withdrawal, has been used to assess the potential of alpha1-adrenoceptor antagonists to cause this side effect.

Male Sprague-Dawley Rats (360–540 g) were anesthetized with metofane. An inguinal skin incision was made on the hind limb of the animal. Both left and right femoral arteries and left femoral vein were isolated and cannulated with PE-50 fluid-filled cannulae for measurement of blood pressure, withdrawal of blood and administration of compound, respectively. The incision site was closed using 9 mm auto-clips. Animals were then placed in Bollman cages with their tails secured with masking tape.

Following recovery from anesthesia, a 1 hour stabilization period was allowed. Four ml of blood are then withdrawn into a heparinized syringe, and the effect on blood pressure and heart rate was noted. Five to seven minutes later the blood was returned to the rat. After another 1 hour stabilization period, test compound or vehicle was administered (i.v.). The blood withdrawal procedure was repeated 10 minutes after administration of vehicle or test compound. Blood pressure and heart rate were monitored continuously throughout the experiment using a Gould polygraph (Model MK200A) and Buxco data acquisition computer system.

Changes in blood pressure following blood withdrawal were compared before and after dosing with test compound.

Proceeding as in Example 21, compounds of Formula (l) were tested for postural hypotension.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:
1. A compound represented by Formula I:

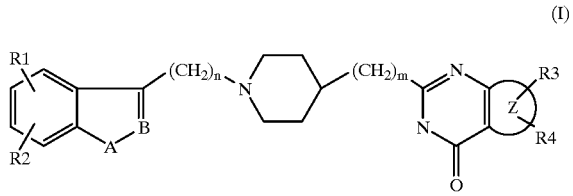

wherein:
A—B is independently in each occurrence NH—C, NH—N, O—C, or S—C;
Ring Z is a pyridine ring;
$R^1$, $R^2$, $R^3$, and $R^4$ are each independently in each occurrence hydrogen, halogen, lower alkyl, lower alkoxy, hydroxy, cyano, nitro, trifluoromethyl, CO—NR'R", NR'R", or NR'—CO—NR'R";
R' and R" are each independently in each occurrence hydrogen or lower alkyl;
m is an integer ranging from 0 to 3 inclusive;
n is an integer ranging from 1 to 6 inclusive; or
pharmaceutically acceptable salts, hydrates or N-oxides thereof.
2. The compound of claim 1 wherein A—B is NH—C.
3. The compound of claim 1 wherein A—B is NH—N.
4. The compound of claim 1 wherein A—B is O—C.
5. The compound of claim 1 wherein A—B is S—C.
6. The compound of claim 1 wherein m is 0.
7. The compound of claim 1 wherein m is 0 and n is 2.
8. The compound of claim 4 wherein m is 0.
9. The compound of claim 4 wherein m is 0 and n is 2.
10. The compound of claim 5 wherein m is 0.
11. The compound of claim 5 wherein m is 0 and n is 2.
12. The compound of claim 2 wherein m is 0.
13. The compound of claim 2 wherein m is 0 and n is 2.
14. The compound of claim 2 wherein $R^1$, $R^2$, $R^3$, and $R^4$ are each independently in each occurrence hydrogen, halogen or lower alkyloxy.
15. The compound of claim 3 wherein m is 0.
16. The compound of claim 3 wherein m is 0 and n is 2.
17. The compound of claim 3 wherein $R^1$, $R^2$, $R^3$, and $R^4$ are each independently in each occurrence hydrogen, halogen or lower alkyloxy.
18. The compound of claim 2 wherein $R^1$, $R^2$, $R^3$, and $R^4$ are each independently in each occurrence hydrogen, halogen or lower alkyloxy.
19. The compound of claim 11 wherein $R^1$, $R^2$, $R^3$, and $R^4$ are each independently in each occurrence hydrogen, halogen or lower alkyloxy.
20. The compound of claim 13 wherein $R^1$, $R^2$, $R^3$, and $R^4$ are each independently in each occurrence hydrogen, halogen or lower alkyloxy.
21. The compound of claim 16 wherein $R^1$, $R^2$, $R^3$, and $R^4$ are each independently in each occurrence hydrogen, halogen or lower alkyloxy.
22. A pharmaceutical composition comprising a therapeutically effective amount of one or more compounds of claim 1.
23. A method of treating a subject which comprises administering to the subject with a disease treatable with an alpha 1A/B antagonist a therapeutically effective amount of one or more compounds of claim 1.
24. The method of claim 23 wherein the disease state comprises disorders of the urinary tract.

25. The method of claim 24 wherein the disease state comprises benign prostatic hypertrophy.

26. The method of claim 23 wherein the disease state comprises pain.

27. The method of claim 26 wherein the disease state comprises inflammatory pain, neuropathic pain, cancer pain, acute pain, chronic pain, or complex regional syndromes.

28. A process for preparing a compound as claimed in claim 1 which process comprises reacting a compound having a general formula

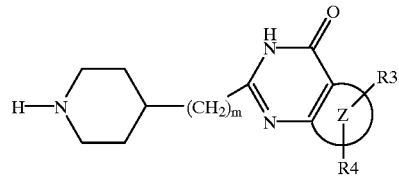

with a compound of general formula

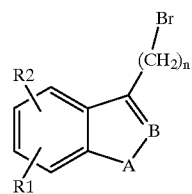

to provide a compound of the general formula

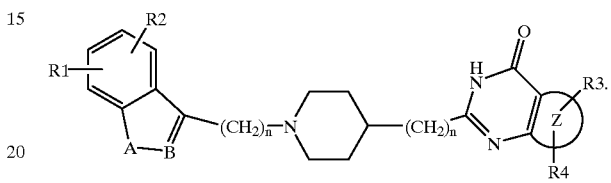

* * * * *